Figure 1:
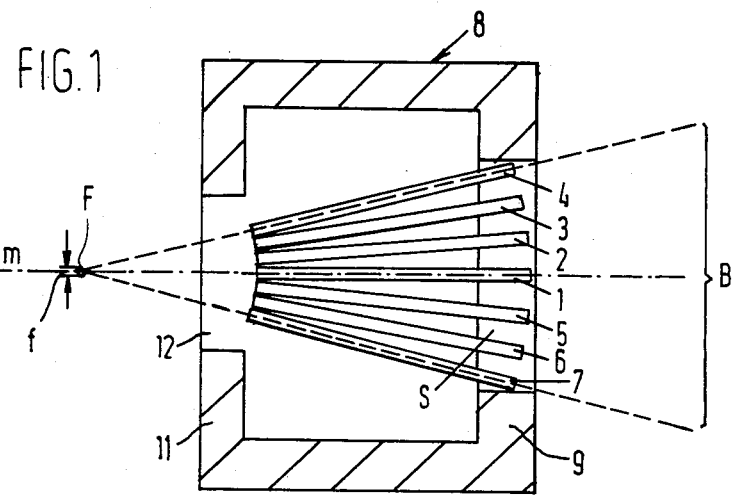

United States Patent [19]
Duinker et al.

[11] Patent Number: 4,741,012
[45] Date of Patent: Apr. 26, 1988

[54] APPARATUS FOR SLIT RADIOGRAPHY

[75] Inventors: Simon Duinker, Bloemendaal; Hugo Vlasbloem, Maasland, both of Netherlands

[73] Assignee: B.V. Optische Industrie "De Oude Delft", Delft, Netherlands

[21] Appl. No.: 821,591

[22] Filed: Jan. 23, 1986

[30] Foreign Application Priority Data

Jan. 29, 1985 [NL] Netherlands ............... 8500244

[51] Int. Cl.$^4$ .............................................. G21K 1/00
[52] U.S. Cl. ................................. 378/145; 378/156; 378/157; 378/147; 378/146
[58] Field of Search ......................... 378/156–158, 378/150–153, 145–148; 250/363 SH

[56] References Cited

U.S. PATENT DOCUMENTS

| | | | |
|---|---|---|---|
| 3,778,614 | 12/1973 | Hounsfield | 378/901 |
| 3,997,794 | 12/1976 | York et al. | 378/150 |
| 4,127,398 | 11/1978 | Singer, Jr. | 378/149 |
| 4,277,685 | 7/1981 | Covic et al. | 378/157 |

FOREIGN PATENT DOCUMENTS

| | | | |
|---|---|---|---|
| 0379243 | 8/1923 | Fed. Rep. of Germany | 378/156 |
| 1493267 | 11/1977 | United Kingdom | 378/147 |
| 0574206 | 9/1977 | U.S.S.R. | 378/147 |
| 0868501 | 10/1981 | U.S.S.R. | 378/147 |

Primary Examiner—Craig E. Church
Assistant Examiner—John C. Freeman
Attorney, Agent, or Firm—Louis E. Marn

[57] ABSTRACT

An apparatus for slit radiography which comprises an X-ray source and a slit diaphragm through which a body to be examined can be scanned by a planar X-ray fan beam. The slit diaphragm is operatively associated with a plurality of juxtaposed tongue-shaped attenuation elements, which elements are arranged for having their free ends swung to a greater or lesser extent into the X-ray beam so as to effect a local attenuation of the beam. The tongue-shaped attenuation elements form at least one flared configuration as seen from the X-ray source.

24 Claims, 4 Drawing Sheets

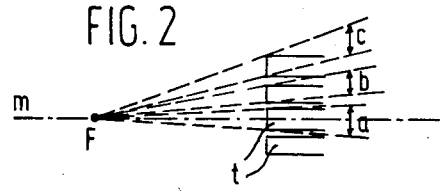
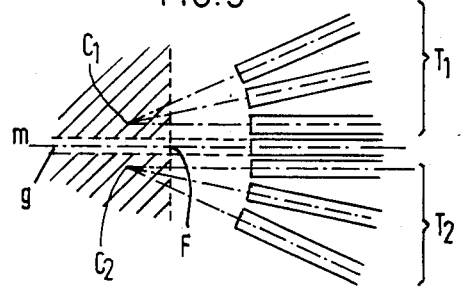
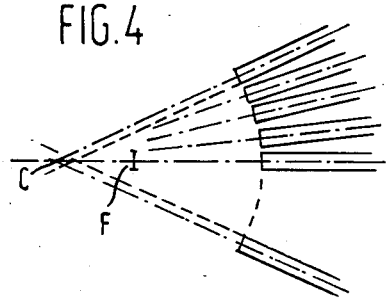
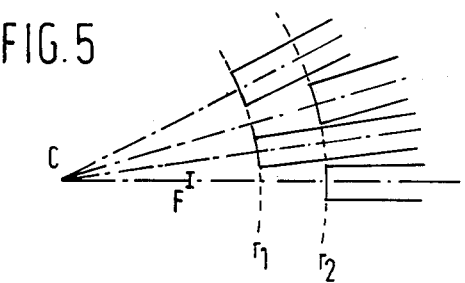
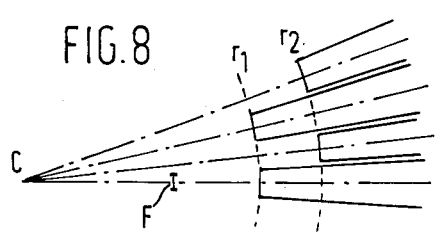
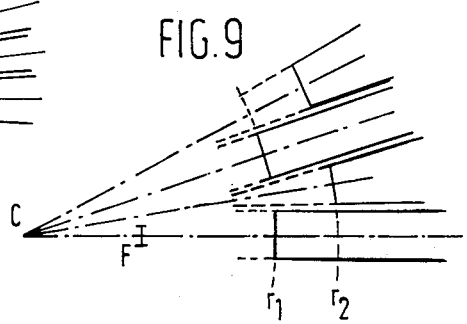

FIG. 10
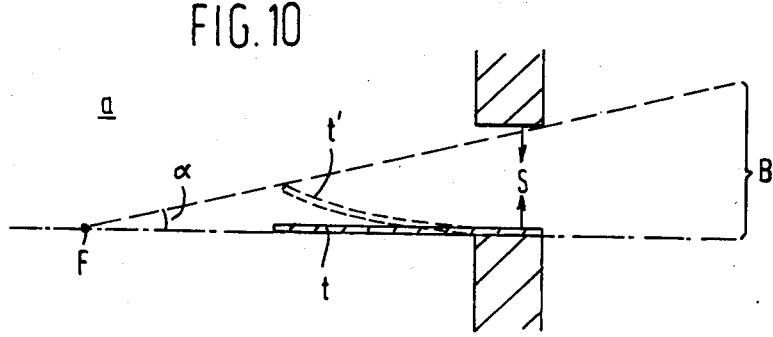
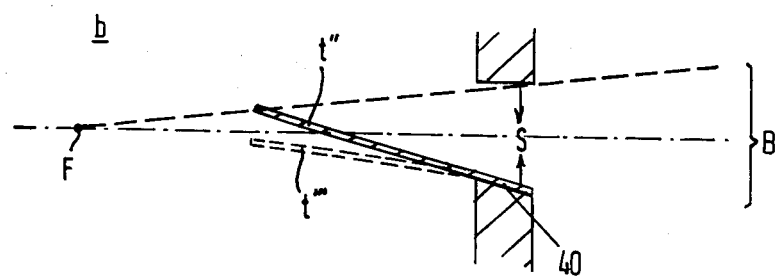
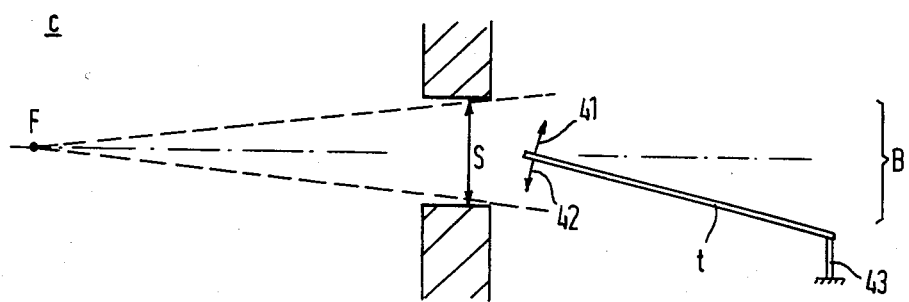
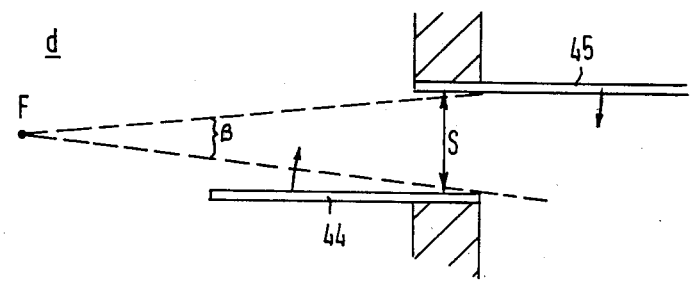

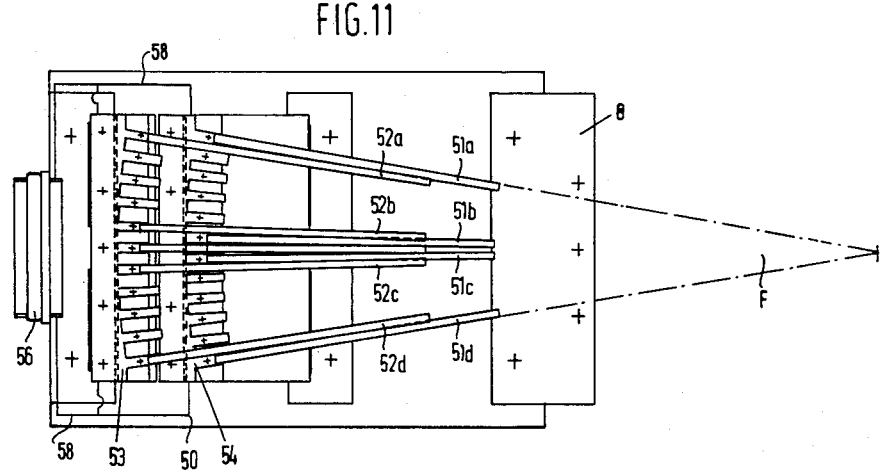
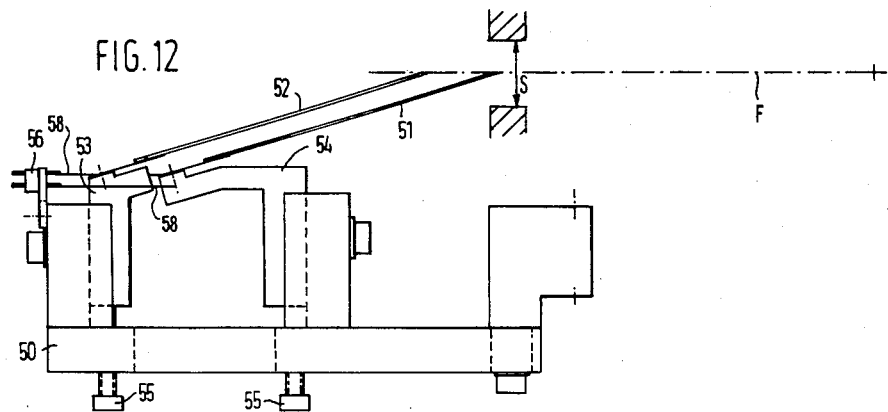

APPARATUS FOR SLIT RADIOGRAPHY

The invention relates to an apparatus for slit radiography comprising an X-ray source and a slit diaphragm through which a body to be examined can be scanned by a planar X-ray fan beam, which diaphragm is operatively associated with a plurality of juxtaposed tongue-shaped attenuation elements arranged for having their free ends swung to a greater or lesser extent into the X-ray beam so as to effect a local attenuation.

Such an apparatus is described in the copending U.S. patent application Ser. No. 713,198.

It is an object of the present invention to enhance the apparatus described in copending U.S. patent application Ser. No. 713,198 by providing a special configuration of tongue-shaped attenuation elements which results in a further improvement of the quantity of the X-ray pictures to be made with the apparatus. Particularly, it is an object of the invention to provide such a configuration of the tongue-shaped attenuation elements that disturbing artefacts, such as stripes, in the image to be formed as caused by the configuration of the attenuation elements are optimally prevented and that the control of the attenuation to be effected by the attenuation elements can be realized in a more effective manner. To this end, in accordance with the invention an apparatus of the above type is characterized in that the tongue-shaped attenuation elements together form a flared configuration as seen from the X-ray source.

The invention will be described in greater detail hereinafter with reference to a number of embodiments and in connection with the accompanying drawing, in which:

FIG. 1 schematically shows in top view an example of a first configuration of tongue-shaped attenuation elements for operative association with a slit diaphragm of an apparatus for slit radiography;

FIG. 2 schematically shows a prior art configuration tongue-shaped attenuation elements;

FIGS. 3-9 schematically show a number of variants of the configuration shown in FIG. 1;

FIGS. 10a-d shows four possible rest positions of the attenuation elements; and

FIGS. 11 and 12 schematically show in top and side view, respectively, a double-deck arrangement of a configuration of tongue-shaped attenuation elements in accordance with the invention.

FIG. 1 schematically shows in top sectional view an example of a configuration of tongue-shaped attenuation elements 1-7 mounted in cantilevered fashion on one of the longer edges of a rectangular slit S formed in a diaphragm housing 8. In the example shown, the diaphragm housing is of rectangular section and slit S is provided in a flat front wall (or diaphragm plate). This wall may, however, have a convex shape as well.

An aperture 12 is provided in the rear wall 11 of the diaphragm housing opposite to slit S. Diaphragm housing 8 is of a material that is impervious to X-rays, such as lead, or is coated with such a material.

An X-ray source schematically indicated by X-ray focus F is mounted rearward of diaphragm housing 8 centrally relative to aperture 12 and slit S. Consequently, the X-ray source can scan in known per se manner a body to be irradiated by means of a planar fan beam B through aperture 12 and slit S. As described in copending U.S. patent application Ser. No. 713,198, during scanning the free ends of the attenuation elements can be swung to a greater or lesser extent into the X-ray beam in a plane normal to that of the drawing under the control of appropriate means in order to locally attenuate the X-ray beam.

It is observed that, in practice, the X-ray beam will not be planar in the mathematical sense of the word. Due to the width of slit S, the thickness of the X-ray beam increases with the distance from the X-ray source, as shown in FIG. 10, where the line connecting the upper edge of slit S with the X-ray source and the line connecting the lower edge of slit S with the X-ray source enclose an angle $\alpha$. This angle $\alpha$ is small, however, so that in this specification the X-ray beam is defined as a planar one.

As further described in copending U.S. patent application Ser. No. 713,198, the tongue-shaped attenuation elements may be strips of piezoelectric material which, if necessary, may additionally be coated with X-ray attenuating material and are fixedly mounted in cantilevered fashion on one of the edges of slit S or on a separate support. By applying a suitable electrical voltage across a piezoelectric strip, the free end thereof can be swung to a greater or lesser extent into the X-ray beam. So-called PXE-5 elements by Philips may be used to advantage for this purpose, which elements contain a lead compound and thus provide sufficient attenuation for permitting a convenient control.

As further described in U.S. patent application Ser. No. 713,199 the tongue-shaped attenuation elements may be of a different suitable material as well, for example spring steel, whether or not coated with an X-ray absorbing material. The position of the free end can be controlled magnetically either directly or through the intermediary of a link coupled to a slidable core of a magnet coil.

In the event that the tongues exhibit no or insufficient flexibility, the tongues have their ends pivotally secured to the edge of the slit or are mounted for pivotal movement about a point intermediate their ends.

It is observed that the tongues may be secured to a separate support 43 (FIG. 10) instead of to the edge of the slit diaphragm. This support may be positioned between slit S and the X-ray source as well as beyond slit S. Decisive is only that the tongues can affect the sector of the X-ray beam from the source as defined by the X-ray focus and the slit.

In the example shown in FIG. 1, the tongue-shaped attenuation elements are of elongate and rectangular shape but are not mounted parallel to each other but in a flared configuration as seen from X-ray focus F. The longitudinal center lines of the tongues intersect the bisectional plane m of beam B approximately at the X-ray focus.

By way of illustration, FIG. 2 schematically shows part of an apparatus employing attenuation tongues t extending parallel to each other. The X-ray focus is designated by F. Furthermore, in FIG. 2 the sectors of the X-ray beam from the X-ray focus that can be affected by the different tongue-dimensions are designated by a, b and c. FIG. 2 makes it clear that the more outward the position of a tongue, the greater the influence of adjacent tongues on the sector controlled, in principle, by the first-named tongue. For example, sector b is not only affected by the associated tongue but also by the adjacent tongue (the uppermost one in FIG. 2) as soon as the latter is swung out of the plane of the drawing by the associated control device. As a result, the process of properly controlling the tongues so that a desired attenuation is achieved in a given sector will be quite complicated.

This problem is solved by the flared configuration of attenuation tongues shown in FIG. 1.

As in FIG. 1 the center lines of the tongues converge in the X-ray focus, unattenuated radiation may get through due to the gaps between the tongue ends facing X-ray focus F and the subsequent wedge-shaped interspaces between the tongues. This effect is even enlarged as X-ray focus F is not of infinitely small dimensions. In practice, the X-ray focus can have a width f of about 0.5 mm.

Due to the finite dimensions of X-ray focus F, the end of each attenuation tongue extending into the X-ray beam corresponds not only with a region of perfect shadow, in which the desired attenuation is achieved, but also with a penumbral region extending in the inevitable, though small, interspaces between the tongues. The radiation passing through such penumbral regions can reach the body to be examined and the subsequent X-ray screen without having been attenuated by the tongues. As a result, the X-radiation passed will exhibit a varying intensity in the plane of the X-ray beam within the beam sector to be affected by a tongue, which should preferably be prevented as much as possible.

In accordance with a further elaboration of the idea underlying the present invention, this gap problem can be diminished by taking a number of measures.

As a first measure, in accordance with the invention the tongues are given a width in excess of the width f of X-ray focus F.

Furthermore, for preference an odd number of attenuation tongues is used with the longitudinal center line of the central tongue extending in the bisectional plane m of beam B.

Finally, a tongue configuration may be used to advantage in which the center lines of the tongues intersect bisectional plane m outside X-ray focus F. A number of tongue configurations embodying these measures will be described hereinafter by way of example.

FIG. 3 shows a configuration of attenuation tongues in which the tongues are divided into groups. Each group has its own point of convergence of the longitudinal center lines of the tongues of that group. By way of example, FIG. 3 shows two of such groups, $T_1$ and $T_2$, located on opposite sides of the central tongue. Groups $T_1$ and $T_2$ each include three tongues in this example. The longitudinal center lines of the tongues of group $T_1$ converge in a point $C_1$ located rearward of X-ray focus F and outside the strip-shaped region G defined by the prolongations of the longitudinal edges of the central tongue. The point of convergence $C_2$ of the center lines of the tongues of group $T_2$ is correspondingly located on the opposite side of bisectional plane m.

FIG. 4 shows a configuration of elongate, rectangular attenuation tongues in which the longitudinal center lines of the tongues all converge in one and the same point C located in bisectional plane m though outside X-ray focus F. In the example shown, point C is located rearward of the X-ray focus. Furthermore, the outermost tongues are so placed that the prolongations of the inner longitudinal edges thereof do not intersect the X-ray focus.

FIG. 5 shows a configuration of elongate, rectangular attenuation tongues in which the longitudinal center lines converge in a manner similar to that shown in FIG. 4 but in which the wedge-shaped spaces between the tongues are reduced as the ends of the tongues facing the X-ray focus are staggered. The tongue ends facing the X-ray focus alternately touch (in the rest position) circles having point of convergence C as the center and a radius $r_1$ and $r_2$, respectively.

It is observed that both in the examples described above and in those to be described hereinafter, the tongues may just as well extend from the edge of slit S or from a separate support into a direction away from X-ray focus F while still arranged in a flared configuration. It is further possible to mount the attenuation tongues on both the upper edge of slit S or a corresponding support and the lower edge of slit S or a corresponding support. In that case and if the tongues extend into the same direction, measures should preferably be taken to prevent the tongues from touching each other. For example, the tongues of one set can be so spaced from each other that the tongues of the other set may, if necessary, swing into the resultant interspaces. It is further possible to mechanically or electrically limit the swing of the tongues. Such steps are not required, however, if one set of tongues extends into the direction of the X-ray focus while the other set extends away from the focus, as shown in FIG. 10d.

In accordance with a further elaboration of the invention, the wedge-shaped interspaces present when using rectangular tongues can be fully avoided by employing elongate attenuation elements tapered wedge-like into the direction of the X-ray focus. Such a configuration is shown in FIG. 6.

Figure 6:
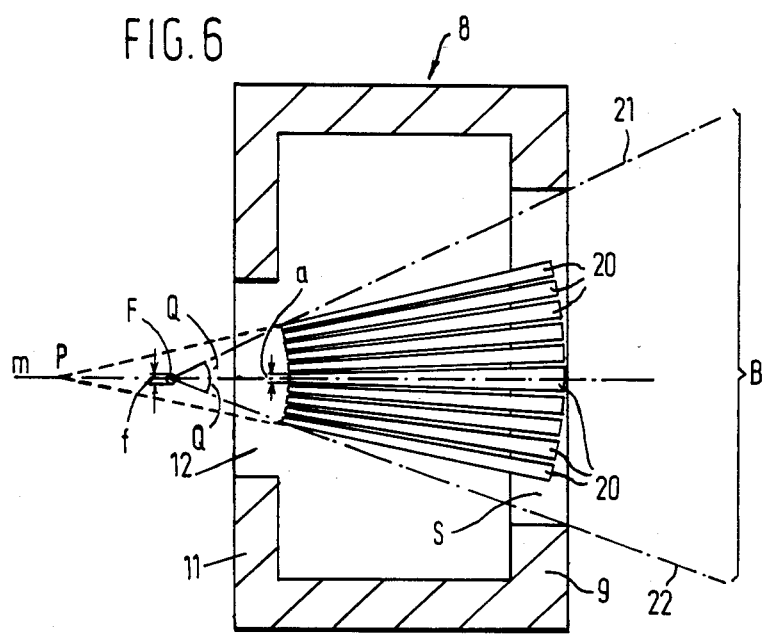

In FIG. 6 the wedged shaped attenuation tongues are designated by 20. The prolongations of the longitudinal edges of the tongues converge to a point in bisectional plane m that is located rearward or forward of the X-ray focus, for example the point designated by P.

The wedge shape of the tongues allows a more effective affection of the X-ray beam, while the convergence of the prolongations of the longitudinal edges of the attenuation tongues in a point P forward or rearward of the X-ray focus results in preventing the free passage of X-rays between adjacent attenuation elements.

Figure 7:
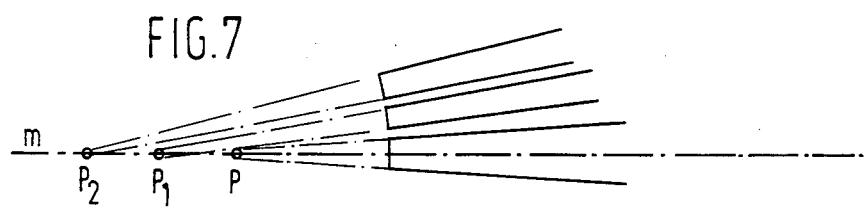

It is observed that the prolongations of the longitudinal edges of the wedge-shaped tongues need not all converge in the same point P. For example, to compensate for a possible intensity variation of the X-radiation as a function of the angle within the fan beam B, it may be expedient to cause the prolongations of the longitudinal edges of certain attenuation tongues or groups of tongues to converge in one or more other points ($P_1$, $P_2$), provided such points be likewise located forward or rearward of X-ray focus F. This is illustrated in FIG. 7.

The width of slit S defines an effective fan angle 2Q (see FIG. 6) of the X-ray fan beam as indicated by marginal rays 21 and 22.

The tongue-shaped attenuation elements are preferably so placed that the longitudinal center line of the central element extends in the bisectional plane m of the fan angle. If this bisectional plane coincides with the medium perpendicular plane of slit S, there should be an odd number of attenuation elements, for example nine or eleven instead of ten.

Furthermore, the width a of the narrow edge of each attenuation element that faces the X-ray focus should again preferably exceed the width f of X-ray focus F. In practice, the width of the X-ray focus can be approximately 0.5 mm, while the width of the narrow edge of the attenuation elements can be, for instance, 1.6 mm.

An additional advantage of the use of wedge-like tapered attenuation tongues over rectangular attenuation tongues is that the former exhibit a higher mechanical resonant eigen-frequency, so that the time of response is shorter and the execution of the scanning of a body to be irradiated via the slit will take less time.

When using wedged shaped attenuation tongues, a staggered configuration of the ends facing the X-ray focus similarly to that shown in FIG. 5 can be employed. Such a configuration is shown in FIG. 8. It is further possible to combine wedged attenuation tongues with rectangular attenuation tongues. FIG. 9 shows such a configuration employing, moreover, staggered ends.

As shown in FIG. 9, a wedged tongue is situated between each two rectangular tongues. In this example the longitudinal center lines of all tongues converge in one and the same point C located rearward of X-ray focus F and the ends of the rectangular tongues are spaced a distance $r_1$ from C while the ends of the wedged tongues are spaced a distance $r_2$ from C, with $r_2 > r_1$. Again, the ends of both types of tongues have a width in excess of width f of X-ray focus F. Self-evidently, the configuration shown in FIG. 9 may be modified so that $r_1 > r_2$.

The attenuation elements can be suitably secured, for instance by soldering, clamping, cementing or screwing, to one of the longer edges of slit S or to a separate support. In the event of the attenuation elements being piezoelectric elements, the lead terminal at the end of each element that is secured to the slit edge or the support is preferably in electrical contact with the diaphragm housing or the support having ground potential.

To prevent sparking between adjacent attenuation tongues when using piezoelectric elements, the tongues may be provided with a thin insulating coating. Furthermore, instead thereof or in combination therewith, the attenuation tongues may be mounted in an enclosure at any rate part of which is transmissive to X-rays, which enclosure is filled with an appropriate gas or liquid for preventing sparking between the tongues. If the tongues are mounted in a diaphragm housing in the manner of FIG. 1, openings 12 and S will then be sealed with plates capable of transmitting X-rays without substantially attenuating same.

FIG. 10 shows four possible ways of positioning the tongue-shaped attenuation elements. In the embodiment of FIG. 10a, in the rest position the tongues t do not essentially extend into X-ray beam B to be passed through the slit diaphragm. During operation, however, the free ends of the tongues can swing upwardly as shown in broken lines at t'.

In the embodiment of FIG. 10b, in the rest position the tongues t" block the entire X-ray beam B to be passed through the slit diaphragm while during operation the free ends of the tongues can swing downwardly to pass a greater or smaller portion of the X-ray beam. The position of the tongues in which the slit is fully exposed is shown in broken lines at t'''. If the tongues are straight in their rest position, in the embodiment illustrated by FIG. 10b the edge on which the tongues are secured should be bevelled as indicated at 40 in this Figure.

FIGS. 10a and 10b show two extreme positions. Self-evidently, an intermediate rest position as shown in FIG. 10c is possible, for instance a position in which half of the beam is intercepted. The amount of radiation passed can be increased or decreased by swinging the tongues from this rest position into the directions indicated by arrows 42 and 41, respectively. In the embodiment of FIG. 10c, the tongues t are not mounted on the edge of the slit diaphragm but on a separate, schematically shown support 43. FIG. 10d shows two sets of tongues 44 and 45, respectively, adapted to swing from opposite edges of slit S into X-ray beam B. One set of tongues 44 faces X-ray focus F whereas the other set 45 points away from focus F. Self-evidently, each of these sets of tongues may be mounted in the manner of FIGS. 10a, 10b or 10c. Moreover, the tongues of one set may be staggered relative to the tongues of the other set.

In the embodiments described above, the gap problem has been diminished by preventing as much unattenuated radiation from passing through the interspaces between the tongues as possible. In these embodiments this is realized, inter alia, by causing the penumbral region corresponding with the end of an attenuation tongue to optimally coincide with the tongue itself or with an adjacent tongue.

Nevertheless, even in the embodiments described a portion of the X-ray beam may escape affection as adjacent tongues are swung to different extents into the beam. For example, one tongue may be in the position indicated by t in FIG. 10a whereas an adjacent tongue may be in the position indicated by t' in FIG. 10a, resulting in a free interspace between these tongues.

In accordance with a further elaboration of the idea underlying the present invention, the effect of such interspaces due to different positions of adjacent tongues can fully or essentially be eliminated by employing a so-called double-deck or multi-deck arrangement of attenuation tongues, in which at least two sets of tongues extend in different planes.

Such an arrangement employing two sets of tongues is shown in FIG. 11 and FIG. 12. FIG. 11 shows a system of attenuation tongues in double-deck arrangement in top view while FIG. 12 shows the arrangement of FIG. 11 in side view. The tongues have their one ends secured to a support 50 and their free ends extend, in the manner of FIG. 10c, into the X-ray fan beam from X-ray focus F to be passed through slit S in diaphragm housing 8.

For clarity, FIG. 11 only shows some tongues 51a ... 51d associated with the lowermost set and some tongues 52a ... 52d associated with the uppermost set. Support 50 is provided with one or more bracket means 53 and 54, respectively, for each set of tongues. In the embodiment shown, the two sets of tongues extend in parallel planes and the tongues of the respective sets extend upwards in an inclined position to one and the same level. This can be readily accomplished by, as shown, mounting bracket means 53 and 54 in horizontal succession on the support and by further employing identical tongues.

In the embodiment shown the tongues are of rectangular shape while the tongues of one set are laterally staggered relative to the tongues of the other set. In this manner, radiation passed in unattenuated form by the lowermost set can effectively be intercepted and attenuated by the tongues of the uppermost set.

The arrangement shown further permits the tongues of each set to be spaced further apart from each other, resulting in a simpler mounting procedure and the absence of insulating problems.

Support 50 is provided with adjusting means 55 for accurately adjusting the height of the tongues with respect to the slit diaphragm. Furthermore, a connector 56 is mounted on support 50 by leads 58 to the corresponding lead terminal of each other piezoelectric strip for the application of the electrical signals controlling the operative positions of the tongues.

It is observed that each one of the sets of tongues may have a configuration as shown in any one of FIGS. 2–9.

It is further observed that different variants of the embodiments shown will be readily obvious to the worker in the art after the foregoing. In the above, reference was already made to the possibility of having the attenuation tongues point away from the X-ray source and the possibility of mounting attenuation means on both edges of the slit or on supports corresponding therewith. Such variants as well as combinations thereof, both in respect of each other and in respect of the embodiments shown, are considered to fall within the scope of the present invention.

We claim:

1. An apparatus for slit radiography, which comprises:
   an X-ray source;
   a slit diaphragm for forming a planar X-ray beam;
   a plurality of juxtaposed elongated attenuation elements positioned along said slit diaphragm each elongated attenuation element having a free end and having means responsive to a detector signal to enable each attenuation element to swing into said x-ray beam in respnse to said control signal, said elongated attenuation elements extending outwardly in flared configuration from said X-ray source.

2. The apparatus according to claim 1, wherein longitudinal center lines of said elongated attenuation elements intersect a bisecting plane (B) of said planar X-ray beam (B) outside of said X-ray source.

3. The apparatus according to claim 1, wherein said elongated attenuation elements are divided into groups and wherein longitudinal center lines of each group intersect a point outside said X-ray source.

4. The apparatus according to claim 1, wherein one of said elongated attenuation elements is mounted with its longitudinal center line in a bisecting plane of said planar X-ray beam.

5. The apparatus according to claim 1, wherein a width of an end of said elongated attenuation elements disposed toward said X-ray source is greater than a dimension of said X-ray source.

6. The apparatus according to claim 3, wherein said elongated attenuation elements are essentially rectangular and said longitudinal center line of each group of said elongated attenuation elements, located on either side of a centrally disposed elongated attenuation element, intersesct at a convergence point located on either side of said longitudinal center line of said centrally disposed elongated attenuation element and in a plane normal to center lines of said elongated attenuation elements, and outside a strip-like region defined by a prolongation of longitudinal sides of said centrally disposed elongated attenuation element.

7. The apparatus according to claim 1, wherein said elongated attenuation elements are essentially rectangular and wherein longitudinal center lines of said elongated attenuation elements converge in a point located in a bisecting plane of a fan angle of said planar X-ray beam on a side X-ray source remote from said elongated attenuation elements, said point being located such that prolongations of inner longitudinal sides of outermost elongated attenuation elements do not intersect at said X-ray source.

8. The apparatus according to claim 3, wherein said elongated attenuation elements are individually tapered toward said X-ray source and wherein prolongations of longitudinal sides of each group of each group of elongated attenuation elements converge at a point located outside said X-ray source in a bisecting plane of said planar X-ray beam.

9. The apparatus according to claim 1, wherein said elongated attenuation elements are divided into two groups, said elongated attenuation elements of one group alternating with said elongated attenuation elements of said other group, ends of said elongated attenuation elements of one group facing said X-ray source being disposed closer to said X-ray source than corresponding ends of said elongated attenuation elements of said other group.

10. The apparatus according to claim 9, wherein elongated attenuation elements of one of said groups are essentially rectangularly-shaped wherein elongated attenuation elements of said other group are essentially wedge-shaped and wherein longitudinal sides of adjacent wedge-shaped and rectangular elongated attenuation elements are essentially parallel.

11. The apparatus according to claim 1, wherein said elongated attenuation elements are mounted to a support in two sets wherein one set of said elongated attenuation elements being mounted so that free ends thereof are swung into said planar X-ray beam from one side of said support and said other set being mounted whereby free ends thereof are swung into said planar X-ray beam from an opposite side of said support.

12. The apparatus according to claim 11, wherein free ends of one set of elongated attenuation elements face said X-ray source and free ends of said other set of said elongated attenuation elements away from said X-ray source.

13. apparatus according to claim 1, wherein said elongated attenuation elements are mounted in a rest position outside of said slit diaphragm.

14. The apparatus according to claim 1, wherein said elongated attenuation elements in a rest position position extend partly into said planar X-ray beam to be passed through said slit diaphragm.

15. The apparatus according to claim 1, wherein said elongated attenuation elements are mounted in an enclosure including a wall formed with said slit diaphragm and wherein an X-ray pervious window is disposed across said slit diaphragm and wherein a wall of said enclosure opposite said wall including said slit diaphragm is provided with an X-ray pervious window proximate to said X-ray source.

16. The apparatus according to claim 15, wherein said elongated attenuation elements are piezoelectric strips and said enclosure is filled with an insulating fluid for preventing sparking between adjacent piezoelectric strips.

17. The apparatus according to claim 1, wherein said elongated attenuation elements are piezoelectric strips each having two lead terminals and wherein one lead terminal of each piezoelectric strip is electrically connected to like lead terminal of each other piezoelectric strip.

18. The apparatus according to claim 1, wherein said elongated attenuation elements are piezoelectric strips provided with an insulating coating.

19. The apparatus according to claim 1, wherein said elongated attenuation elements are divided into two sets extending in different planes and wherein free ends of said elongated attenuation elements extending obliquely into said planar X-ray beam.

20. The apparatus according to claim 19, wherein said elongated attenuation elements of one set are laterally staggered relative to said elongated attenuation elements of said other set.

21. The apparatus according to claim 19, wherein each set of elongated attenuation elements is mounted to a bracket means spatially disposed from one another on a common support with respect to said X-ray source.

22. The apparatus according to claim 21, wherein said common support is provided with means for adjusting position of said common support relative to said slit diaphragm.

23. The apparatus according to claim 21, wherein said elongated attenuation elements are piezoelectric strips and wherein said common support is provided with a connector for application of electrical signals to said piezoelectric strips.

24. The apparatus according to claim 4 wherein there is provided an odd number of elongated attenuation elements.

* * * * *